United States Patent
Chowhan et al.

(10) Patent No.: US 6,224,911 B1
(45) Date of Patent: May 1, 2001

(54) PROCESS FOR THE PREPARATION OF ENTERIC COATED PHARMACEUTICAL DOSAGE FORMS

(75) Inventors: Zakauddin T. Chowhan, Sunnyvale; Patrick H. Vo, San Diego, both of CA (US)

(73) Assignee: Syntex (U.S.A.) LLC, Palo Alto, CA (US)

( * ) Notice: Subject to any disclaimer, the term of this patent is extended or adjusted under 35 U.S.C. 154(b) by 0 days.

(21) Appl. No.: 08/375,049

(22) Filed: Jan. 18, 1995

(Under 37 CFR 1.47)

Related U.S. Application Data

(63) Continuation of application No. 08/038,597, filed on Mar. 16, 1993, now abandoned.

(51) Int. Cl.[7] .................................................. A61K 9/32
(52) U.S. Cl. ..................... 424/490; 424/462; 424/474; 424/475; 424/482; 424/497; 427/2.21
(58) Field of Search ................................. 424/474, 475, 424/482, 490, 497, 462; 427/2.21

(56) References Cited

U.S. PATENT DOCUMENTS

| | | |
|---|---|---|
| 4,017,647 * | 4/1977 | Ohno et al. ........................ 424/482 |
| 4,377,568 | 3/1983 | Chopra . |
| 4,556,552 * | 12/1985 | Porter et al. ...................... 424/482 |
| 4,704,295 * | 11/1987 | Porter et al. ...................... 424/482 |
| 4,816,259 * | 3/1989 | Matthews et al. ................. 424/463 |
| 4,837,030 * | 6/1989 | Valorose, Jr. et al. ............ 424/456 |
| 4,857,337 * | 8/1989 | Miller et al. ...................... 424/482 |
| 4,970,081 * | 11/1990 | Frisbee .............................. 424/482 |
| 5,047,258 * | 9/1991 | Belanger et al. ................. 424/482 |
| 5,102,668 * | 4/1992 | Eichel et al. ...................... 424/490 |
| 5,167,964 * | 12/1992 | Muhammad et al. ............. 424/482 |
| 5,213,794 * | 5/1993 | Fritsch et al. .................... 424/482 |
| 5,229,134 * | 7/1993 | Mention et al. .................. 424/482 |
| 5,330,759 * | 7/1994 | Pagay et al. ...................... 424/462 |
| 5,851,579 * | 12/1998 | Wu et al. ......................... 427/2.21 |

FOREIGN PATENT DOCUMENTS

| | | |
|---|---|---|
| 0 072 021 | 2/1983 | (EP) . |
| 59-193382A | 11/1984 | (JP) . |

OTHER PUBLICATIONS

Rowe, R.C.., (1981) *J. Pharm. Pharmacol.* 33: 423.

* cited by examiner

*Primary Examiner*—Robert H. Harrison
(74) *Attorney, Agent, or Firm*—Heller Ehrman White & McAuliffe LLP

(57) ABSTRACT

This invention is directed to a process for the preparation of enteric coated pharmaceutical dosage forms. This invention is further directed to the aqueous enteric coating dispersions suitable for use in the process and the enteric coated pharmaceutical dosage forms prepared by the process.

13 Claims, No Drawings

PROCESS FOR THE PREPARATION OF ENTERIC COATED PHARMACEUTICAL DOSAGE FORMS

CROSS-REFERENCE TO RELATED APPLICATION

This application is a continuation of our application Ser. No. 08/038,597, filed Mar. 16, 1993, and now abandoned.

FIELD OF THE INVENTION

This invention relates to a process for preparing enteric coated pharmaceutical dosage forms, to the aqueous enteric coating dispersions suitable for use in the process, and to the enteric coated pharmaceutical dosage forms prepared by the process.

BACKGROUND OF THE INVENTION

The absorption of a drug as it passes through the alimentary canal can be controlled by coating the pharmaceutical with a substance which will at certain pH values retard release of the drug while at other pH values promote disintegration and/or leaching of the drug from the dosage form. For example, a coat comprised of an anionic polymer such as cellulose acetate phthalate prevents premature disintegration of the pharmaceutical in the acidic environment of the stomach and promotes rapid release of the drug in the intestine. Such a coat is commonly called an enteric coat (e.g., see U.S. Pat. No. 4,857,337 for a description of enteric coated aspirin dosage forms).

The enteric coat surrounds the core dosage form with a film which is hydrophobic at acidic pH values. At pH values below 4, the monolayers of the film are arranged in a compact alignment resistant to penetration by water and ions. However, at pH values of 5.8 and more basic the monolayers expand allowing the penetration of water and ions.

The enteric coat is applied by coating the pharmaceutical dosage form with a liquid enteric coating mixture in the presence of a sufficient amount of heat to vaporize the solvents. The mixture usually contains, in addition to an anionic polymer, a plasticizer or a combination of plasticizers. The plasticizers cross-link the polymer molecules together by hydrogen bonding which results in a lattice structure that adds tensile strength to the esoteric coat and promotes adhesion to the surface of the dosage form. The enteric coat can contain other ingredients such as surfactants, pigments, and fillers.

Organic solvents or aqueous mixtures of organic solvents are often used to prepare the enteric coating mixtures (e.g., see U.S. Pat. No. 4,377,568 for a description of aqueous alcoholic enteric coating dispersions). However, organic solvents have to be recycled and can result in contamination of the enteric coat. When water is used to prepare an enteric coating dispersion, a detackifier and glidant (e.g., talc) may be needed to avoid sticking or clumping of the pharmaceutical dosage forms during the application process. Constant and vigorous stirring is usually required to prevent the anionic detachifier/glidant from settling out. Because of the stirring, foaming may occur and antifoam agents may be necessary.

The solubility of an anionic polymer in an aqueous solvent can be increased by adding base (e.g., see Japanese Kokai No. J5 9193-382-A for a description of an aqueous enteric coating solution of carboxymethylethyl cellulose and base). However, the free base that is present in the solvent will also then be present in the resulting enteric coat and the capacity of the coat to resist disintegration in an acidic environment is reduced.

In addition to the various process-related problems which can occur during the application of the enteric coat, other problems may become apparent after the coat has dried (e.g., see Rowe, R. C. (1981) *J Pharm Pharmacol* 33: 423). A sufficient amount of enteric coating material must be applied to the uncoated dosage form to assure the formation of an adequate enteric coat. However, as the amount of the enteric coating material is increased, problems may occur as a result of the internal stress that develops in the coat as it dries. For example, a common problem associated with enteric coated tablets is logo-bridging (i.e., the enteric coat pulls away from a tablet surface and the legibility of the monogram is lost). Typically, logo-bridging occurs when the weight gain due to the enteric coat exceeds 2–3% of the uncoated tablet weight.

The disclosure of the above and other documents referred to throughout this application are incorporated herein by reference.

SUMMARY OF THE INVENTION

This invention comprises a process for preparing enteric coated pharmaceutical dosage forms, which process comprises combining in water one or more anionic polymers, one or more plasticizers, one or more optional excipients, and a volatile base to form an aqueous enteric coating dispersion; and coating an uncoated pharmaceutical dosage form with the aqueous dispersion.

This invention also comprises an aqueous enteric coating dispersion suitable for use in the preparation of enteric coated pharmaceutical dosage forms, the dispersion comprising one or more anionic polymers, one or more plasticizers, one or more optional excipients, and a base which promotes the dispersion of the anionic polymers in water but readily vaporizes during the coating process.

This invention also comprises an enteric coated pharmaceutical dosage form prepared by the process of this invention.

ADVANTAGES OF THE INVENTION

The process of this invention produces an enteric coat which is free of organic solvents, detackifiers, glidants, and antifoam agents. In addition, because a volatile base is used in the process to promote the solubility of the anionic polymer in the aqueous enteric coating dispersion, the resulting enteric coat does not contain free base.

The process of this invention produces enteric coated tablets that at 6 to 15% weight gain pass USP enteric coating specifications for disintegration and dissolution and do not exhibit logo-bridging.

DETAILED DESCRIPTION OF THE INVENTION

Definitions

Unless otherwise stated, the following terms used in the specification and claims have the meanings given below:

All percentages refer to percentages by weight.

The term "volatile base" means a base which which will readily vaporize under the conditions used for coating the uncoated dosage form.

The term "aqueous dispersion" or "aqueous enteric coating dispersion" means a mixture of enteric coating material dispersed in a solvent consisting essentially of water.

The term "enteric coating material" means the non-aqueous ingredients that are present in the aqueous enteric coating dispersion and the materials which comprise the enteric coat. For the process of this invention such materials can include anionic polymers, plasticizers, and optional excipients.

The term "pharmaceutically acceptable" means that which is generally safe, non-toxic and neither biologically nor otherwise undesirable and includes that which is acceptable for veterinary use as well as human pharmaceutical use.

The term "pharmaceutical dosage form" means a dosage form of a drug (e.g., tablet, powder, capsule, and the like) which is pharmaceutically acceptable, as defined above, and which possesses the necessary and desirable characteristics of a dosage form acceptable for administration to a patient (e.g., a tablet of acceptable hardness, dissolution, stability, and a size and weight practical for oral administration).

The term "optional excipients" means that excipients may or may not be present. For example, "combining in water one or more anionic polymers, one or more plasticizers, one or more optional excipients, and a volatile base" means that combining the excipients may or may not be carried out in order for the described process to fall within the invention.

The term "uncoated" when referring to a dosage form means that the dosage form does not have an enteric coat.

Materials

Suitable anionic polymers for the enteric coating of this invention are insoluble in acidic environments (e.g., gastric juice) but are soluble at pH 5.5 and upwards. Such polymers include cellulose acetate phthalate, methacrylate-base polymers, cellulose acetate, trimellitate, hydroxypropyl methylcellulose phthalate, and the like. Suitable methacrylate-based polymers include Eudragit® L and Eudragit® S, anionic polymers synthesized from methacrylic acid and an acrylate. Specific methacrylate-based polymers include Eudragit® L 100, which is synthesized from methacrylic acid and methyl methacrylate and has a ratio of free carboxyl groups to ester groups of approximately 1:1, Eudragit® L 100-55, which is synthesized from methacrylic acid and ethyl acrylate and has a ratio of free carboxyl groups to ester groups of approximately 1:1, and Eudragit® S 100, which is synthesized from methacrylic acid and methyl methacrylate and has a ratio of free carboxyl groups to ester groups of approximately 1:2.

Generally, the anionic polymers useful in this invention are dissolved in organic solvents before being used in a film coating process. For example, the solvents recommended by the manufacturer for dissolving Eudragit® L and S polymers include methyl alcohol, ethyl alcohol, ethyl alcohol/water, isopropyl alcohol, isopropyl alcohol/water, n-butyl alcohol, propylene glycol, ethyleneglycol monobutyl ether, acetone, acetone/isopropyl alcohol, and the like. However, base will promote the dispersion of these anionic polymers in water; and a suitable volatile base (e.g., ammonium hydroxide) will readily vaporize under the conditions used for the film coating process of this invention.

Suitable plasticizers impart sufficient tensile strength to the coating to prevent film cracking and logo-bridging. Such plasticizers include triethyl citrate, dibutyl phthalate, polyethylene glycols, propylene glycol, diethylphthalate, acetyl triethyl citrate, and the like.

Suitable optional excipients include surfactants (e.g., polysorbate 80, sodium lauryl sulfate, and the like), colorants (e.g., iron oxide, lakes, dyes, titanium dioxide, and the like), and fillers (e.g., microcrystalline cellulose and the like).

Drugs which are useful in this invention include any for which enteric adsorption might be desirable. Exemplary drugs include naproxen (see U.S. Pat. No. 4,009,197) and ketorolac (see U.S. Pat. No. 4,089,969) and the pharmaceutically acceptable salts thereof. While, suitable pharmaceutically acceptable dosage forms of drugs can be prepared by any of the usual and acceptable modes known in the art, the preferred dosage form is a tablet (e.g., see Edward Rudnic and Joseph B. Schwartz. 1990. *Remington's Pharmaceutical Sciences,* ed. A. R. Gennaro, 1633–65, Easton: Mack Publishing Company, for a description of how to make tablet forms of drugs).

In some instances it may be necessary to apply a sealing coat to the tablet prior to applying the enteric coat. A sealing coat protects the tablet ingredients from the water in the aqueous enteric coating dispersion to assure the stability of the dosage form. The sealing coat comprises a resin such as shellac, zein, and the like and is applied to the dosage form by methods known to those of ordinary skill in the art.

Description

An anionic polymer or a combination of anionic polymers is dispersed in water and the dispersion is stirred. A volatile base is slowly added and the dispersion is further stirred.

A plasticizer or a combination of plasticizers is emulsified in water and the emulsion is stirred. The emulsion is then added to the dispersion of polymer and base. One or more optional excipients are then added. The aqueous dispersion is then passed through a #80 mesh screen to produce the final aqueous dispersion which is suitable for use in the preparation of an enteric coated pharmaceutical dosage form. The preparation of an aqueous enteric coating dispersion of this invention is described in Example 1.

Preferably the anionic polymer is polymethacrylate-based, preferably Eudragit® L 100-55 alone or in combination with Eudragit® L 100; the plasticizer is triethyl citrate and dibutyl phthalate either alone or triethyl citrate in combination with dibutyl phthalate or polyethylene glycol 400; and the base is ammonium hydroxide. Preferably the dispersion comprises 7 to 18% Eudragit® L 100-55, 0 to 8% Eudragit® L 100, 0 to 6% triethyl citrate, 0 to 6% dibutyl phthalate, and 0.3 to 1.0% ammonium hydroxide; more preferably 7 to 8% Eudragit® L 100-55, 7 to 8% Eudragit® L 100, 2 to 3% triethyl citrate, 1 to 2% dibutyl phthalate, and 0.3 to 0.9% ammonium hydroxide.

The enteric coat can be applied by coating a cascading bed of the uncoated pharmaceutical dosage form with the aqueous enteric coating dispersion in the presence of a sufficient amount of heat to vaporize the water and base. Unless a water-insoluble excipient (e.g., iron oxide) has been included, the dispersion does not require stirring during the application process. Thus, without relying upon organic solvents, lubricants, or antifoam agents, the enteric coating material is delivered to the pharmaceutical dosage form with uniform coverage and the coating material dries without adjacent dosage forms adhering together.

The aqueous enteric coating dispersion of this invention is particularly suited for application by spray coating. Preferably, the pharmaceutical dosage form is a tablet. The tablet is loaded into a coating pan (e.g., Freund model HCT-30 Hicoater) which is preheated by inlet air temperature until the target exhaust temperature is reached. While the pan is rotating, the aqueous enteric coating dispersion is sprayed onto the tablets using a spray gun (e.g., a Freund model HM with a 1.5 mm fluid nozzle). After the spraying is completed the tablets are dried for an additional period.

The preparation of an enteric coated tablet by the process of this invention is described in Example 2.

The disintegration characteristics of the enteric coated tablets of this invention can be determined using the in vitro methods described in *The United States Pharmacopeia* (USP XXII). Rockville, Md.: United States Pharmacopeial Convention, Inc., 1990, pp 1577–1578. Dissolution characteristics can be determined by in vitro methods described in USP XXII, pp 1578–1579. In vitro disintegration and dissolution tests of enteric coated tablets prepared by the process of this invention is described in Examples 3 and 4, respectively.

Enteric coated tablets prepared by the process of this invention pass USP enteric coating specifications for disintegration and dissolution at as low as 6 to 8% film coat weight gain. No logo-bridging occurs at as high as 15% film coat weight gain.

EXAMPLES

The following examples are not intended to limit the scope of the invention. While the process parameters provided are meant to reflect a certain level of accuracy, some experimental error and deviation should be tolerated.

Example 1

Preparation of Aqueous Enteric Coating Dispersion

Eudragit® L 100-55 (70.0 gms) and Eudragit® L 100 (70 g) were dispersed in purified water (500 g) and the suspension was stirred for approximately 10 minutes. Strong ammonia solution, NF (8.4 g; 9.3 mL of 28–29% $NH_3$ in water) was slowly added to the dispersion and the mixture was stirred for 30 minutes. Triethyl citrate, NF (28 g) and dibutyl phthalate (11 g) were emulsified in water (269 g) and the emulsion was stirred for 10 minutes. The emulsion was added to the dispersion containing the Eudragit® polymers and base, and the resulting dispersion was moderately stirred for 20 minutes. The dispersion was passed through a #80 mesh screen to produce an aqueous enteric coating dispersion comprising the following:

| | % |
|---|---|
| Dispersion 1 | |
| Eudragit ® L 100-55 | 7.32 |
| Eudragit ® L-100 | 7.32 |
| Triethyl Citrate, NF | 2.93 |
| Dibutyl Phthalate | 1.17 |
| Strong Ammonia Solution, NF | 0.88 |
| Purified Water, USP | 80.4 |

Proceeding similarly, the following aqueous enteric coating dispersions were prepared:

| | % |
|---|---|
| Dispersion 2 | |
| Eudragit ® L-100-55 | 7.31 |
| Eudragit ® L-100 | 7.31 |
| Triethyl Citrate, NF | 2.93 |
| Dibutyl Phthalate | 1.17 |
| Strong Ammonia Solution, NF | 0.87 |
| Iron Oxide | 0.40 |
| Purified Water, USP | 80.0 |
| Dispersion 3 | |
| Eudragit ® L 100-55 | 7.30 |
| Eudragit ® L 100 | 7.30 |
| Triethyl Citrate, NF | 4.17 |
| Strong Ammonia Solution, NF | 0.87 |
| Purified Water, USP | 80.3 |
| Dispersion 4 | |
| Eudragit ® L 100-55 | 7.38 |
| Eudragit ® L 100 | 7.38 |
| Triethyl Citrate, NF | 3.69 |
| Polyethylene Glycol 400, NF | 0.53 |
| Strong Ammonia Solution, NF | 0.88 |
| Purified Water, USP | 80.1 |
| Dispersion 5 | |
| Eudragit ® L 100-55 | 14.9 |
| Dibutyl Phthalate | 2.97 |
| Strong Ammonia Solution, NF | 0.38 |
| Purified Water, USP | 81.8 |
| Dispersion 6 | |
| Eudragit ® L 100-55 | 17.8 |
| Dibutyl Phthalate | 5.09 |
| Strong Ammonia Solution, NF | 0.80 |
| Purified Water, USP | 76.3 |
| Dispersion 7 | |
| Eudragit ® L 100-55 | 14.6 |
| Triethyl Citrate, NF | 4.18 |
| Strong Ammonia Solution, NF | 0.65 |
| Purified Water, USP | 80.5 |
| Dispersion 8 | |
| Eudragit ® L 100-55 | 14.6 |
| Triethyl Citrate, NF | 2.09 |
| Dibutyl Phthalate | 2.09 |
| Strong Ammonia Solution, NF | 0.66 |
| Purified Water, USP | 80.5 |
| Dispersion 9 | |
| Eudragit ® L 100-55 | 16.4 |
| Dibutyl Phthalate | 3.32 |
| Strong Ammonia Solution, NF | 0.68 |
| Purified Water, USP | 79.6 |
| Dispersion 10 | |
| Eudragit ® L 100-55 | 14.7 |
| Dibutyl Phthalate | 4.19 |
| Strong Ammonia Solution, NF | 0.65 |
| Purified Water, USP | 80.5 |

Example 2

Preparation of Enteric Coated Tablets

In this Example, naproxen sodium tablets were chosen as the model pharmaceutical dosage form. Uncoated naproxen sodium tablets pretreated with a sealing coat were loaded into a Freund model HCT-30 Hicoater coating pan which had been preheated at an inlet air temperature of 70° C. until the exhaust temperature was 44° C. While the pan was rotated at 10 rpm, Dispersion 1 was sprayed onto the tablets using a Freund model HM spray gun with a 1.5 mm fluid nozzle at an atomizing pressure of 2.8 kg/cm$^2$ and a flow rate of 6.0 mL/min.

After spraying was completed, the tablets were dried for an additional 10 to 20 minutes. The enteric coated naproxen sodium tablets prepared from Dispersion 1 had 5.5% weight gain.

Proceeding as above, but at a pan speed of 20 to 22 rpm, inlet temperature of 50° C., exhaust temperature of 33° C., atomizing pressure of 2.2 kg/cm², and a flow rate of 6.5 mL/min, enteric coated naproxen sodium tablets were prepared from Dispersion 2.

Proceeding as above, but at a pan speed of 10 rpm, inlet temperature of 80° C., exhaust temperature of 42 to 43° C., atomizing pressure of 2.6 kg/cm², and a flow rate of 6.0 mL/min, enteric coated naproxen sodium tablets with 7.8% weight gain were prepared from Dispersion 3.

Proceeding as above, but at a pan speed of 10 to 12 rpm, inlet temperature of 70° C., exhaust temperature of 42 to 43° C., atomizing pressure of 2.5 to 3.0 kg/cm², and a flow rate of 6.0 to 6.3 mL/min, enteric coated naproxen sodium tablets with 6.1% weight gain were prepared from Dispersion 4.

Proceeding as above, but at a pan speed of 15 rpm, inlet temperature of 75° C., exhaust temperature of 43° C., atomizing pressure of 2.6 kg/cm², and a flow rate of 6.2 mL/min, enteric coated naproxen sodium tablets with 8.0% weight gain were prepared from Dispersion 5.

Proceeding as above, but at a pan speed of 13 rpm, inlet temperature of 70° C., exhaust temperature of 40.5° C., atomizing pressure of 2.5 kg/cm², and a flow rate of 6.2 mL/min, enteric coated naproxen sodium tablets with 6.5% weight gain were prepared from Dispersion 6.

Proceeding as above, but at a pan speed of 12 to 15 rpm, inlet temperature of 70° C., exhaust temperature of 44 to 45° C., atomizing pressure of 2.8 kg/cm², and a flow rate of 6.0 mL/min, enteric coated naproxen sodium tablets with 8.0% weight gain were prepared from Dispersion 7.

Proceeding as above, but at a pan speed of 12 to 15 rpm, inlet temperature of 68° C., exhaust temperature of 42 to 44° C., atomizing pressure of 3.0 kg/cm², and a flow rate of 5.0 mL/min, enteric coated naproxen sodium tablets with 6.0% weight gain were prepared from Dispersion 8.

Proceeding as above, but at a pan speed of 18 rpm, inlet temperature of 70° C., exhaust temperature of 40° C., atomizing pressure of 2.5 kg/cm², and a flow rate of 6.2 mL/min, enteric coated naproxen sodium tablets with 7.5% weight gain were prepared from Dispersion 9.

Proceeding as above, but at a pan speed of 12 rpm, inlet temperature of 75° C., exhaust temperature of 40.5° C., atomizing pressure of 2.5 kg/cm², and a flow rate of 6.2 mL/min, enteric coated naproxen sodium tablets with 7.2% weight gain were prepared from Dispersion 10.

Example 3

In Vitro Disintegration Test

Six open-ended transparent tubes (7.5 cm in length and 21.5 mm in diameter) were assembled in a rack such that the bottom of each tube was positioned against a 10-mesh No. 23 (0.025-inch) W. and M. gauge woven stainless-steel wire cloth. The rack was suspended in a 1000 mL low-form beaker in such a manner so that the tubes could be raised and lowered in the imersion fluid at a rate of 29 to 32 cycles per minute through a distance of 5.3 to 5.7 cm. The volume of the imersion fluid was such that the wire mesh is 2.5 cm from the surface of the fluid at the top of the upward stroke and 2.5 cm from the bottom of the beaker at the bottom of the downward stroke.

An enteric coated naproxen sodium tablet was placed in each of the six tubes. The rack was imersed in simulated gastric fluid test solution (see USP XXII, p 1788) maintained at 37° C. and the apparatus was operated for 1 hour. The rack was removed and a perforated plastic cylinder (9.5 mm in length and 20.7 mm in diameter) was added to each tube. The rack was imersed in simulated intestinal fluid test solution (see USP XXII, p 1789) maintained at 37° C. and the apparatus was operated for 2 hours.

The enteric coated naproxen sodium tablets prepared by the process of this invention and tested by the above methods were in compliance with USP specifications for disintegration of enteric coated tablets.

Example 4

In Vitro Dissolution Test

An enteric coated naproxen sodium tablet was placed in a round bottom, 1000 mL vessel containing a dissolution fluid which was maintained at 37° C. and continually stirred at 50 rpm by a paddle held in a horizontal position near the bottom of the container. The dissolution fluid was 0.1 N HCl for the first two hours and 0.1 M phosphate buffer (pH 7.4) for a third hour. Samples of the dissolution fluid were removed at various intervals, filtered through a $8.0\mu$ filter and the amount of dissolved drug was determined by ultraviolet spectrophotometry at 272 nm.

The enteric coated naproxen sodium tablets demonstrated excellent physical resistance to the acid medium (e.g., no dissolution occurred after 2 hours). At pH 7.4, all tablets were in compliance with USP specifications for dissolution of enteric coated tablets.

While the process of this invention has been described with reference to a general description and to specific embodiments by example, it should be understood that various modifications and/or substitutions are possible without departing from the true spirit and scope of the invention.

We claim:

1. A process for preparing an enteric coated pharmaceutical dosage form comprising:

(1) combining in water one or more anionic polymers being synthesized from methacrylic acid and an acrylic acid ester, one or more plasticizers selected from triethyl citrate and dibutyl phthalate, and ammonium hydroxide to form an aqueous enteric coating dispersion free of organic solvents, detackifiers, glidants, and antifoam agents; and (2) spray coating an uncoated pharmaceutical dosage form with the dispersion.

2. The process of claim 1 in which the polymers are a first polymer alone, the first polymer being synthesized from methacrylic acid and ethyl acrylate and having a ratio of free carboxyl groups to ester groups of approximately 1:1, or the first polymer in combination with a second polymer, the second polymer being synthesized from methacrylic acid and methyl methacrylate and having a ratio of free carboxyl groups to ester groups of approximately 1:1.

3. The process of claim 2 in which the dispersion comprises 7 to 8% of the first polymer, 7 to 8% of the second polymer, 2 to 3% triethyl citrate, 1 to 2% dibutyl phthalate and 0.8 to 0.9% ammonium hydroxide.

4. The process of claim 3 in which the pharmaceutical dosage form is a pharmaceutically acceptable naproxen or naproxen sodium tablet.

5. The process of claim 3 in which the pharmaceutical dosage form is a pharmaceutically acceptable ketorolac tablet.

6. An aqueous enteric coating dispersion free of organic solvents, detackifiers, glidants, and antifoam agents and suitable for use in the preparation of an enteric coated pharmaceutical dosage form, the dispersion prepared by combining in water one or more anionic polymers being synthesized from methacrylic acid and an acrylic acid ester, one or more plasticizers selected from triethyl citrate and dibutyl phthalate, and ammonium hydroxide.

7. The dispersion of claim 6 in which the polymers are a first polymer alone, the first polymer being synthesized from methacrylic acid and ethyl acrylate and having a ratio of free carboxyl groups to ester groups of approximately 1:1, or the first polymer in combination with a second polymer, the second polymer being synthesized from methacrylic acid and methyl methacrylate and having a ratio of free carboxyl groups to ester groups of approximately 1:1.

8. The dispersion of claim 7 comprising 7 to 8% of the first polymer, 7 to 8% of the second polymer, 2 to 3% triethyl citrate, 1 to 2% dibutyl phthalate and 0.8 to 0.9% ammonium hydroxide.

9. An enteric coated pharmaceutical dosage form prepared by a process comprising:

(1) combining in water one or more anionic polymers being synthesized from methacrylic acid and an acrylic acid ester, one or more plasticizers selected from triethyl citrate and dibutyl phthalate, and ammonium hydroxide to form an aqueous enteric coating dispersion free of organic solvents, detackifiers, glidants, and antifoam agents; and (2) spray coating an uncoated pharmaceutical dosage form with the dispersion.

10. The enteric coated dosage form of claim 9 in which the polymers are a first polymer alone, the first polymer being synthesized from methacrylic acid and ethyl acrylate and having a ratio of free carboxyl groups to ester groups of approximately 1:1, or the first polymer in combination with a second polymer, the second polymer being synthesized from methacrylic acid and methyl methacrylate and having a ratio of free carboxyl groups to ester groups of approximately 1:1.

11. The enteric coated dosage form of claim 10 in which the dispersion comprises 7 to 8% of the first polymer, of the second polymer, 2 to 3% triethyl citrate, 1 to 2% dibutyl phthalate and 0.8 to 0.9% ammonium hydroxide.

12. The enteric coated dosage form of claim 11 in which the pharmaceutical dosage form is a pharmaceutically acceptable naproxen or naproxen sodium tablet.

13. The enteric coated dosage form of claim 11 in which the pharmaceutical dosage form is a pharmaceutically acceptable ketorolac tablet.

* * * * *